US006221666B1

(12) United States Patent
Clarke et al.

(10) Patent No.: US 6,221,666 B1
(45) Date of Patent: Apr. 24, 2001

(54) METHOD AND APPARATUS FOR CYTOPLASMIC LOADING USING AN IMPACT-MEDIATED PROCEDURE

(75) Inventors: Mark S. F. Clarke, League City; Rob G. Lucas-Dean, San Leon; Daniel L. Feeback, Houston, all of TX (US); Charles R. Vanderburg, Newton, MA (US); Michael M. Withey, Pearland, TX (US)

(73) Assignee: Oceaneering International, Inc., Houston, TX (US)

( * ) Notice: Subject to any disclaimer, the term of this patent is extended or adjusted under 35 U.S.C. 154(b) by 0 days.

(21) Appl. No.: 09/094,548

(22) Filed: Jun. 12, 1998

(Under 37 CFR 1.47)

(51) Int. Cl.$^7$ .................................................. C12N 15/87
(52) U.S. Cl. .................. 435/459; 435/283.1; 435/285.1; 435/285.3; 435/286.6
(58) Field of Search ..................................... 435/440, 459, 435/283.1, 285.1, 286.1, 286.6

(56) References Cited

PUBLICATIONS

Clarke et al. Biotechniques. vol. 17(6), pp. 1118–1125, 1994.*

Takeuchi et al. Plant Molecular Biology. vol. 18, pp. 835–839, 1992.*

* cited by examiner

*Primary Examiner*—James Ketter
*Assistant Examiner*—Irem Yucel
(74) *Attorney, Agent, or Firm*—Kurt S. Myers

(57) ABSTRACT

The present invention is directed to the method and apparatus for the cytoplasmic loading of macromolecules into living cells by an impact-mediated procedure that impacts the cells with a predetermined number of solid particles in a blast of propellant gas. More specifically, the present invention is directed to an impact-mediated procedure that is altered by gravitational conditions and is preferably carried out under hypergravity conditions.

Further, the present invention is directed to an IML method and apparatus for consistently and reproducibly loading macromolecules into the cytoplasm of living cells via membrane wounding at significantly higher efficiencies than can be accomplished using existing methodologies. The IML procedure directs a blast of propellant gas through a rupturable membrane on which solid particles are supported in order to achieve insertion of a predetermined number of particles into the propellant blast. Another preferred embodiment is a particle containment shell that includes a particle support membrane that ruptures at a predetermined propellant blast pressure and has a predetermined number of particles resting on the surface of the support membrane.

25 Claims, 15 Drawing Sheets

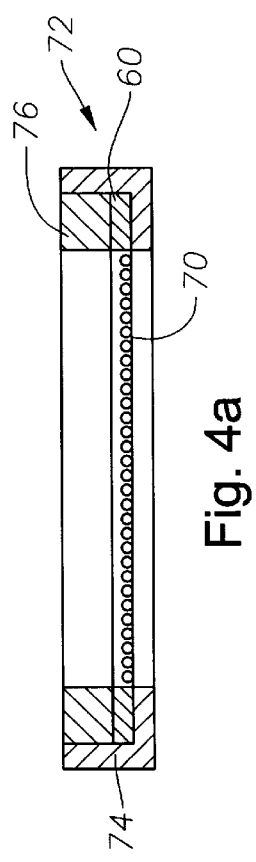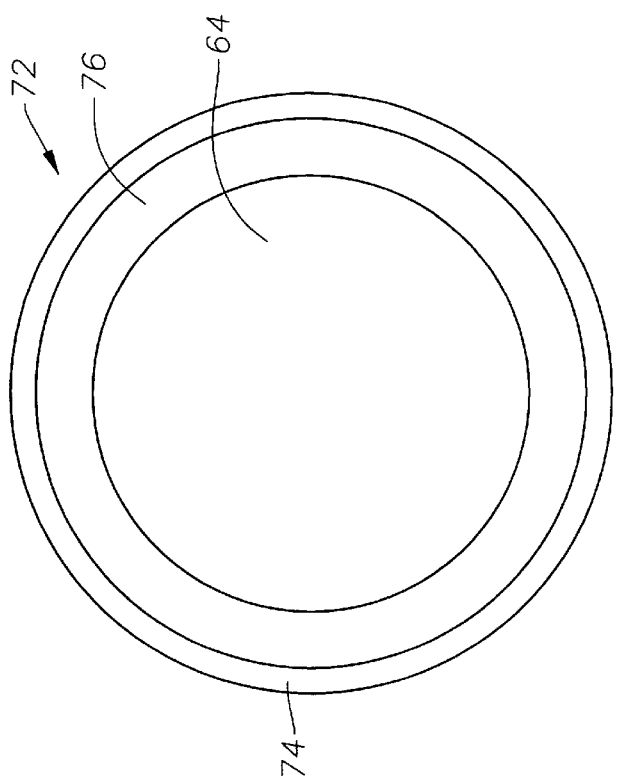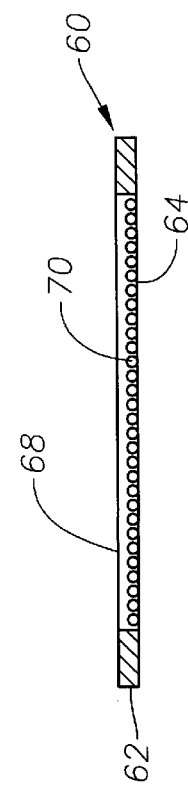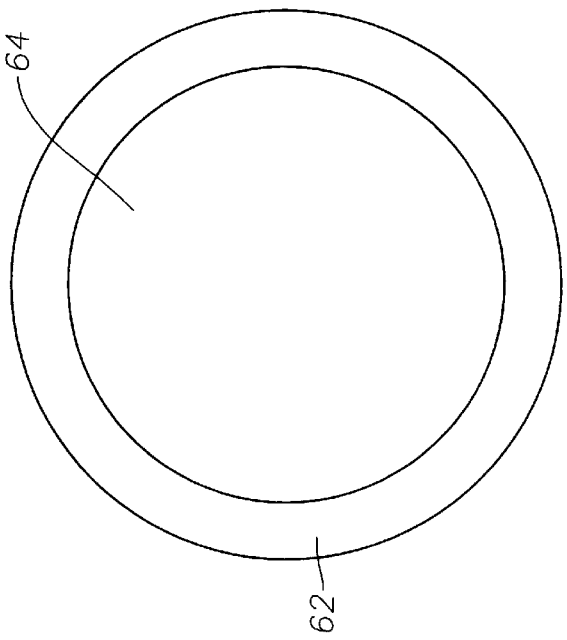

US 6,221,666 B1

METHOD AND APPARATUS FOR CYTOPLASMIC LOADING USING AN IMPACT-MEDIATED PROCEDURE

This invention was made with United States government support, and the U.S. government has a paid-up license and the right in limited circumstances to require the patent owner to license others on reasonable terms.

BACKGROUND OF THE INVENTION

1. Field of the Invention

The present invention is directed to methods and apparatus for cytoplasmic loading using an impact-mediated procedure or "cell wounding" as a means of gaining direct entry to the cell protoplasm.

2. Description of the Related Art

A common approach in modern cell or molecular biology is to insert macro-molecules (e.g., dyes, proteins, nucleic acids) directly into the cytoplasm of living cells to monitor or modify specific cellular processes. Several existing techniques, such as electroporation and biolistics are used nearly exclusively for transfection (e.g., the loading of plasmid DNA constructs). Other transfection techniques, such as liposome fusion-based methods, exhibit limited transfection efficiencies, appear to work well with only a few cell types and have little utility for loading other macromolecules such as immunoglobulins or dyes. Microinjection, although the most direct and quantitative method of delivering a wide range of macromolecules to the cytoplasm of different cell types, is time consuming, requires specialized equipment and is impractical for loading large numbers of cells. Several simple and inexpensive cell-loading techniques, based on the use of mechanical force to transiently permeabilize the plasma membrane, achieve loading of adherent eukaryotic cells without the need for expensive and/or complex apparatus. These cell-loading techniques, scrape loading, scratch loading, bead loading, and syringe loading, have demonstrated the utility of "cell wounding" as a means of gaining entry to the cell cytoplasm.

A more detailed description of bead loading as a "cell wounding" technique is set forth in an article "Cytoplasmic Loading of Dyes, Protein and Plasmid DNA Using an Impact-Mediated Procedure" by Mark S. F. Clarke et al., BioTechniques, Vol.17, No.6 (1994), pp 1118–1125, which is incorporated herein by reference. A detailed description of the method of fluorescent flow cytometry to determine a mean fluorescence value is set forth in the article.

SUMMARY OF THE INVENTION

The present invention is directed to the method and apparatus for the cytoplasmic loading of macromolecules into living cells by an impact-mediated procedure that impacts the cells with a predetermined number of solid particles in a blast of propellant gas. More specifically, the present invention is directed to an impact-mediated procedure that is altered by gravitational conditions and is preferably carried out under hypergravity conditions.

Further, the present invention is directed to an IML method and apparatus that directs a blast of propellant gas through a rupturable membrane on which solid particles are supported, in order to achieve insertion of a predetermined number of particles into the propellant blast. Another preferred embodiment is a particle containment shell that includes a particle support membrane that ruptures at a predetermined propellant blast pressure and has a predetermined number of particles resting on the surface of the support membrane.

BRIEF DESCRIPTION OF THE DRAWINGS

The drawings are a part of the written description of the present invention and are understood to provide a more full and clear description of the invention. It is to be noted, however, that the appended drawings illustrate specific embodiments of the invention and are not to be considered limiting of the scope of the invention. The invention may have embodiments that are of equally equivalent configurations, e.g., mechanical vs. solid state electronic.

FIGS. 3A and 3B are a particle containment shell that holds the particles for the preferred embodiment of the present invention; included is a top view (3B) and a cross-sectional view (3A) showing the particles;

FIGS. 4A and 4B illustrate the "bullet" for the preferred embodiment and the construction of the "bullet"; included is a top view (4B) and an expanded cross-sectional side view (4A);

DESCRIPTION OF THE PREFERRED EMBODIMENTS

Figure 2:
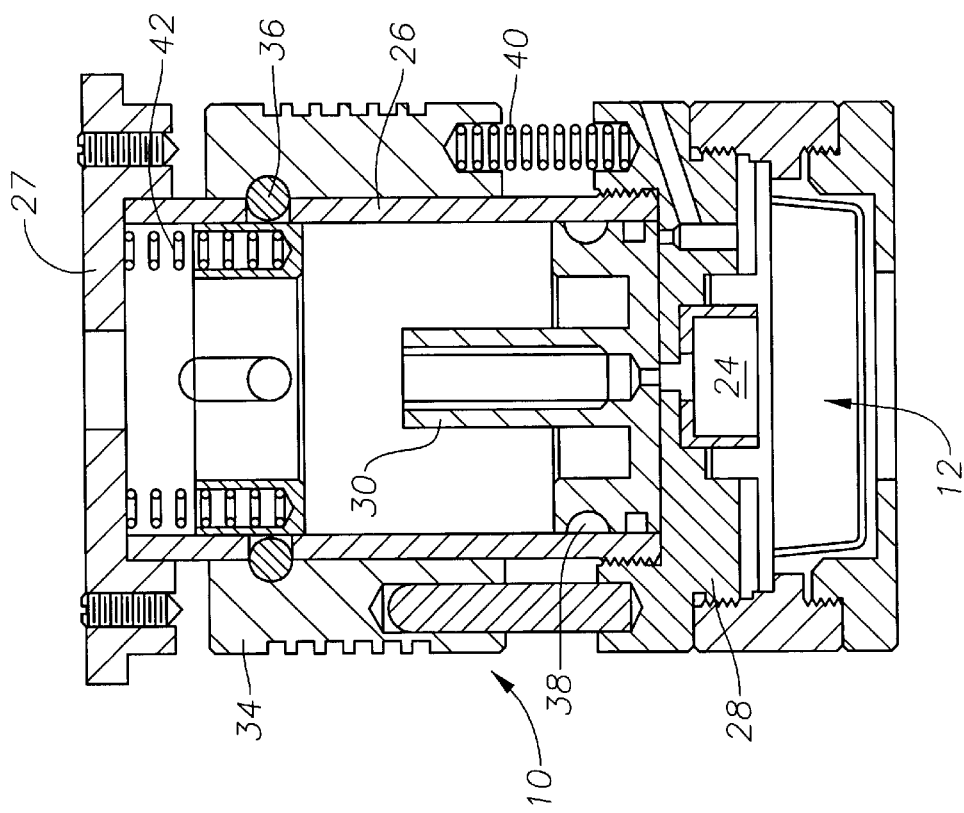
FIG. 2 is a cross-section of the preferred embodiment of a particle-blasting device of the present invention in the fired position.

For the purpose of the present application certain terms are defined:

"IML" shall mean impact-mediated loading.

"Cell wounding" shall mean that wound to a living cell that is impacted, and survives at least 16 hours after being impacted, by a particle or particles for loading a macromolecule into the cell.

"Particle containment shell" shall mean a member that supports a predetermined number of particles on a rupturable membrane.

"Blast pressure" shall mean the measured pressure of a blast of propellant gas used in the IML procedure at the point of measurement.

"Bullet" shall mean the structure to hold the "particle containment shell" and having the shape to fill a bullet chamber in an IML device.

"kD" shall mean kilo-Dalton.

"$\mu$m" shall mean microns or $1/1,000$ millimeter.

"0 xg" shall mean microgravity; "1 xg" means terrestrial gravity; "greater than 1 xg" means hypergravity.

"MW" shall mean molecular weight.

The IML Procedure

The procedure of the present invention, IML, allows a large number of adherent cells (ca. 20000–30000 cells) to be loaded at the same time and is applicable to loading all soluble macromolecules, such as dyes, proteins and plasmid DNA constructs directly into the cell cytoplasm. A significant drawback to permeating cells by mechanical wounding by other methods has been cell loss due to failure of the plasma membrane to reseal in the case of large wounds. The problem of extensive cell death has been overcome by IML by i) creating wounds that are of uniform size below a threshold that is lethal to the cell and ii) performing the loading at hypergravity that may eliminate the need of a surfactant molecule to treat the cells prior to wounding for the purpose of enhancing resealing.

The present invention is directed to the procedures and apparatus that provide a controllable and reproducible method for the production of transient plasma membrane wounds in adherent tissue-cultured cells of various types. In this regard, the cells treated with the IML procedure of the present invention may be human, animal or plant cells. The specific conditions may vary depending on the kind of cell; however, common to all cells treated is the object to efficiently perform the procedure under controllable and reproducible conditions.

The IML procedure of the present invention uses a solid particle. A large variety of particles may be used such as ceramics, glass, organic and inorganic crystals, metals, inorganic and organic granules, non-biodegradable polymers and biodegradable polymers. Specific examples are glass beads; metals or cat gut (a biodegradable polymer). When done in a laboratory, a preferable particle is glass beads; however, if the method were carried out in vivo, a biodegradable material may be preferred. A significant aspect of the present invention is that the number and the size of the particles is controlled and known in each procedure or protocol. The number of particles is maintained consistent by placing the particles in a containment shell having a determined shape and volume. The preferred shape of the containment shell has an area about the same size as the culture well containing the cells to be treated. The particles range in size from 5 micron to 500 micron and the size is selected depending on the size of the macromolecule that is to be loaded into the cell, i.e., the larger the macromolecule the larger the particle. The size of the particle is important to overcoming the problem of extensive cell death by creating a more consistent wound that is uniform in size. It is understood, however, that a single protocol is not possible since the protocol must take into account the nature of the cell (human, animal or plant and even more specifically the kind of human, animal or plant cell) and the size of the macromolecule that is being loaded into the cell. One aspect of the present invention is that once a protocol has been established to load a specific cell (human, animal or plant) with a specific macromolecule, that the IML method of the present invention will carry out that protocol in a consistent, controlled and reproducible manner. Another aspect of the present invention is that apparatus of the present invention is designed to accomplish this objective of carrying out the IML method in a consistent, controlled and reproducible manner. Another aspect of the present invention is that a sterile or clean gas is preferably employed for providing the blast of the particles. A preferred gas is nitrogen; however, other inert gases or clean air may be used.

The following examples illustrate several of the key variables of the IML procedure of the present invention:

The examples show (1) that cell survival rate will decrease as blast pressure (i.e. a measure of particle velocity) increases; (2) that the mean fluorescence value (MFV) of individual wounded cells (i.e. those which contain the fluorescent wound marker) will increase with blast pressure, but that the overall MFV of the surviving cell population will decrease due to a greater percentage of the individual particle impacts resulting in cell death rather than membrane wounding; and (3) that if particle size, particle impact velocity and wound marker concentration remain constant, the amount of membrane wound marker which enters the cytoplasm of the wounded cell will decrease relative to the molecular size of the wound marker (i.e. for a given membrane wound size which is open for a particular time period, the number of wound marker molecules which can pass through the plasma membrane wound into the cell cytoplasm is inversely proportional to the molecular size of the wound marker). In these examples glass beads are used.

EXAMPLE 1

Effect of Bead Impact Velocity on Cell Survival

Figure 7:
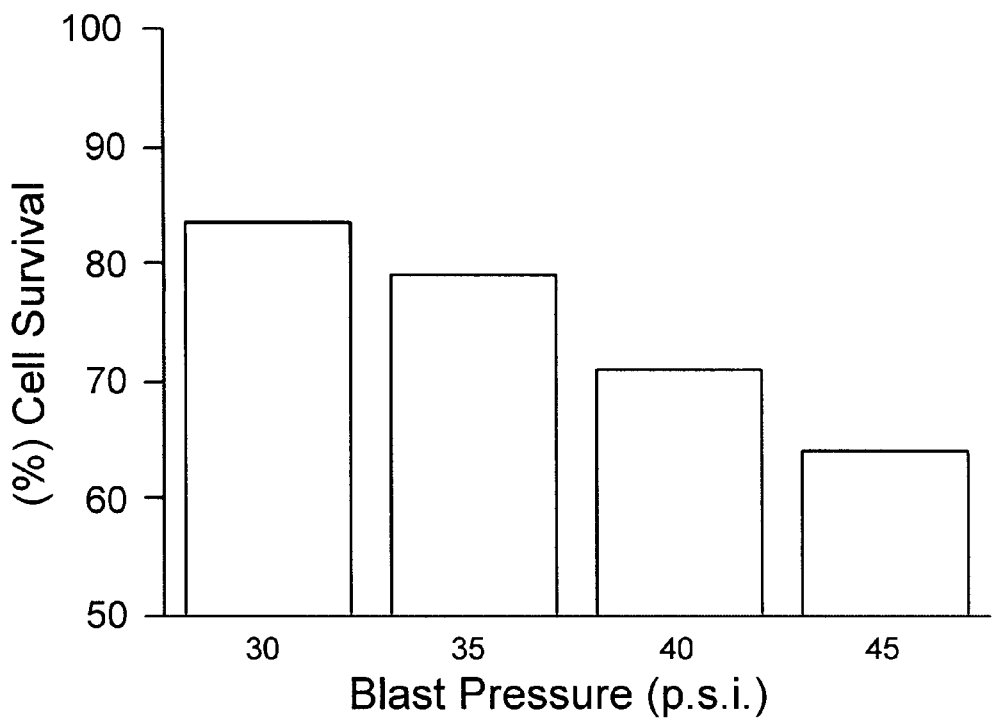
FIG. 7 is a bar graph showing the effect of human cell survival vs. bead blast pressure.

In FIG. 7, the effect of bead impact velocity (as a function of blast pressure) on human myoblast survival is shown. Cell survival is expressed as a (%) relative to the number of cells present in control samples which were treated in an identical fashion to the test cultures but which were not impacted with glass beads. Cell number was determined by measuring cellular DNA. (Bead size=8 $\mu$m dia.; n=20 per condition).

The results show a preferred blast pressure between 15 and 45 p.s.i. where over 65% survival of mammalian cells is obtained.

EXAMPLE 2

Effect of Bead Velocity on Mean Fluorescence Value

Figure 8:
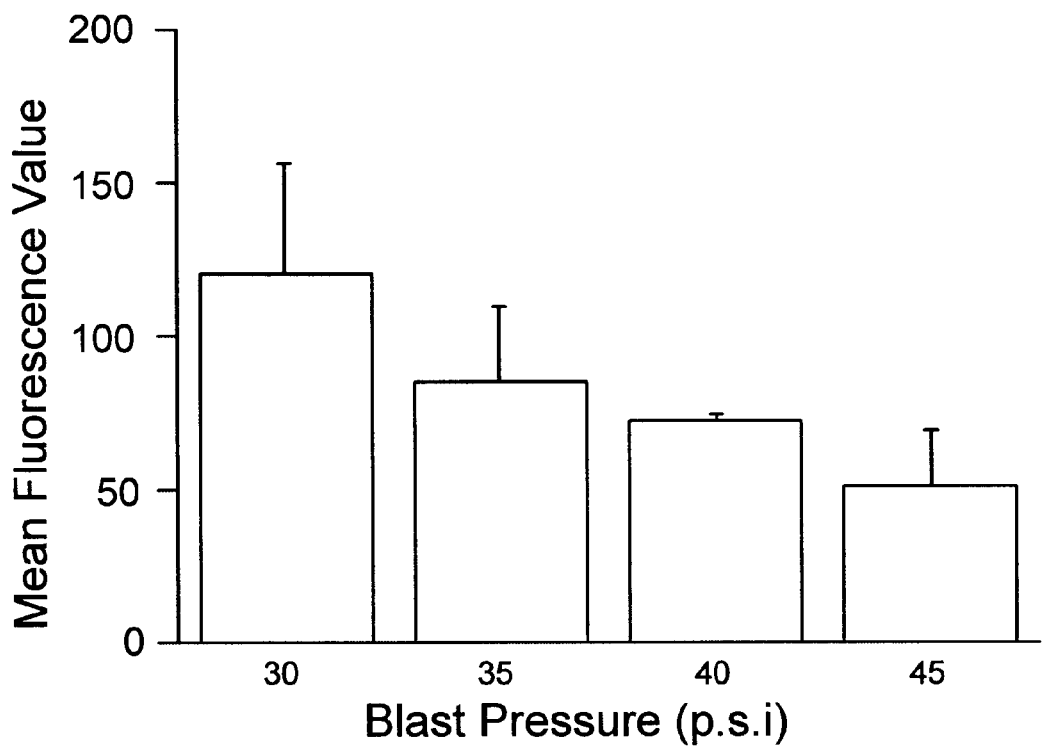
FIG. 8 is a bar graph showing the effect of human cell Mean Fluorescence Value vs. bead blast pressure.

In FIG. 8, the effects of bead impact velocity (as a function of blast pressure) on human myoblast mean fluorescence value (MFV) after impact mediated loading is shown. Cells were loaded in the presence of a fluorescently labeled membrane wound marker (0.2 mM FDx, MW–10 kD). Cells were washed with fresh culture medium and harvested after a further 16 hr in culture to ensure that only the surviving population were analyzed. MFV was determined using fluorescent flow cytometry as previously described (Clarke et al., 1994, above). (Bead size 8 $\mu$m dia.; n=6 per condition).

This example illustrates that the average cell loading of surviving cells is decreased with increased blast pressure.

EXAMPLE 3

Effect of Macromolecule Size

As pointed out herein above, a single protocol is not used to carry out the IML procedure in that the size of the macromolecule to be loaded into the cell has a significant effect. The larger the size of the macromolecule the more difficult is the loading and a larger bead may be used.

Figure 9:
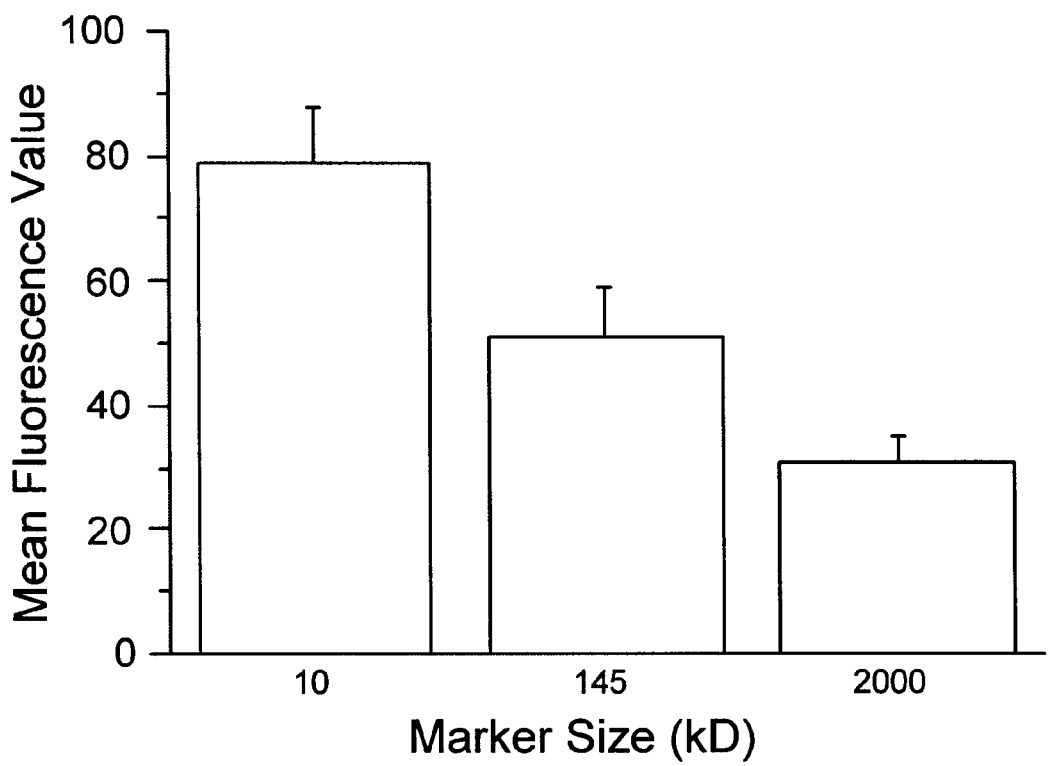
FIG. 9 is a bar graph showing the effect of human cell Mean Fluorescence Value vs. Marker Size.

In FIG. 9, the effects of altering membrane wound marker size on human myoblast mean fluorescence value (MFV) after impact mediated loading is shown. Cells were loaded in the presence of 0.2 mM FDx (MW–10 kD, 145 kD and 2000 kD) under identical IML conditions. Cells were washed with fresh culture medium and harvested after a further 16 hr in culture to ensure that only the surviving population was analyzed. MFV was determined using fluorescent flow cytometry as previously described (Clarke et al., 1994, above). (Bead size=8 μm dia.; Blast Pressure 35 psi; n=8 per condition).

The IML Device

Figure 1:
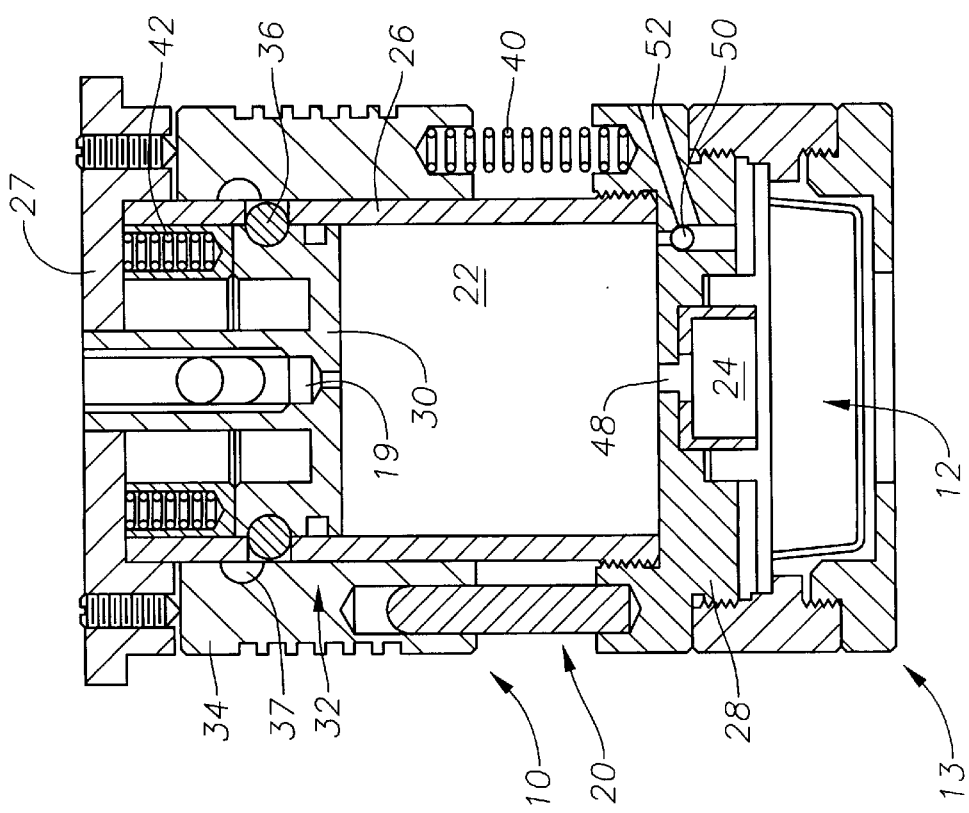
FIG. 1 is a cross-section of a preferred embodiment of an impact-mediated loading device of the present invention.

Referring now to FIGS. 1 and 2, a preferred IML device 10 is illustrated. The device 10 comprises essentially two basic elements, (a) a culture plate 12, having one or more wells in which the living cells that are to be treated and the macromolecules to be loaded are placed, and (b) a particle blasting device 20. The culture plate 12 may be mounted on a stand 13 or structure that secures the dish so that a propellant gas blast containing a predetermined number of particles is directed into the well or wells containing the cells and macromolecules. Although the cross-section shows only one plate, the plate 12 may be a single structure or a plurality of structures and each plate 12 may have a single or plurality of culture wells. The living cells and the desired macromolecule are prepared and inserted into one or more culture wells. The macromolecule is usually in solution and the cells to be treated are in solution or adhere to the bottom of the culture well.

The stand 13 may be assembled and connected to the particle blasting device 20 and then the plate 12 inserted horizontally or assembled starting with the stand and then the plate 12 and finally the bead blasting device 20. The stand 13 also represents any structure for securing the device 20 and it is to be understood that the IML device 10 may be employed in or on a structure other than a bench top as will be described in more detail herein below.

The preferred particle blasting device 20 comprises two gas-connected chambers, a gas chamber 22 for propellant gas and a bullet chamber 24. Preferably, the gas chamber 22 is constructed from a hydraulic cylinder tube 26 that is sealed by a head 27 and a base 28. In the embodiment of FIG. 1, a piston 30 is within the cylinder tube 26 (showing the piston 30 in the raised or cocked position). A firing mechanism 32 surrounds the tube 26.

The firing mechanism 32 of the embodiment of FIG. 1 includes the following structure: a sleeve 34 that surrounds the tube 26, balls 36, detents 37 in the sleeve 34, detents 38 in the piston 30, a first compression spring or springs 40 between the base 28 and the sleeve 34 and a second compression spring or springs 42 inside the tube 26 and between the head 27 and the piston 30. As is shown in FIG. 1, the cocked position, the piston 30 is maintained in the raised position by balls 36 engaging the detents 38 in piston 30 and by the sleeve 34 which surrounds the tube 32. The sleeve 34 is maintained in a raised position by the force of spring(s) 40. The gas chamber 22 is filled with a propellant gas in the cocked position of FIG. 1 through a one way refill valve 19.

Moving the sleeve 34 against springs 40 fires the particle blasting device 20 of this embodiment. When the detents 37 in the sleeve 34 align with the balls 36, the balls 36 move out of detents 38 in the piston 30 and into the detents 37 in the sleeve 34. The piston 30 is then driven within the tube 26 to the base 28 by the force of compressed spring(s) 42. The firing of the piston 30 causes a blast of propellant gas.

The blast of propellant gas is forced out of chamber 22 and through an opening 48 in the base 28 into the bullet chamber 24. The dimensions of chamber 22 in the cocked position, the size of the opening 48 will be fixed for any device; however, the size and compressive force of spring 42 can be varied to obtain a desired range of propellant blast pressures. To control the pressure of the blast of propellant gas into the bullet chamber 24, some gas may be forced though a pressure regulating valve 50 and a passageway 52 in base 28. A particle containment shell is placed into the bullet chamber 24 and receives the propellant gas blast.

Now referring to FIG. 3, a particle containment shell 60 of the present invention is illustrated. The particle containment shell 60 comprises a rigid support ring 62 with a lower rupturable membrane 64. Preferably, the membrane is made of a material and thickness such that the threshold tear strength is at the desired propellant gas blast pressure. A retaining membrane 68 may be applied to the top of the support ring 62. Both membranes 64 and 68 may be affixed or maintained on support ring 62 by adhesives. The particles 70 are applied to the surface of the rupturable membrane 64 in a volatile solvent or as a "dust" prior to the placement of the retaining membrane 68. A desired number of particles may be reproducibly placed on the rupturable membrane 64 by taking a fixed aliquot of a known concentration of the particles in a volatile solvent or of a known weight of particles. The particles 70 are preferably applied to the membrane 64 as a monolayer and cover an area that is essentially the same area as that area the cells fill in the culture well of a culture plate 12.

Referring now to FIG. 4, a bullet 72 of the present invention is illustrated. Bullet 72 holds particle containment shell 60 in an outer casing 74 with particles 70 supported on the rupturable membrane 64. A retaining ring 76 is placed over the particle containment shell 60 to hold the shell 60 in the casing 74. The outside dimensions of the casing 74 are essentially the same dimensions as the inner dimensions of the bullet chamber 24 of the IML device 10. In the preferred embodiment, the predetermined numbers of particles are placed into the blast of propellant gas and are directed to the cells to be treated. Using these preferred conditions the number and size of the particles placed into the blast are controllable and reproducible.

Figure 5:
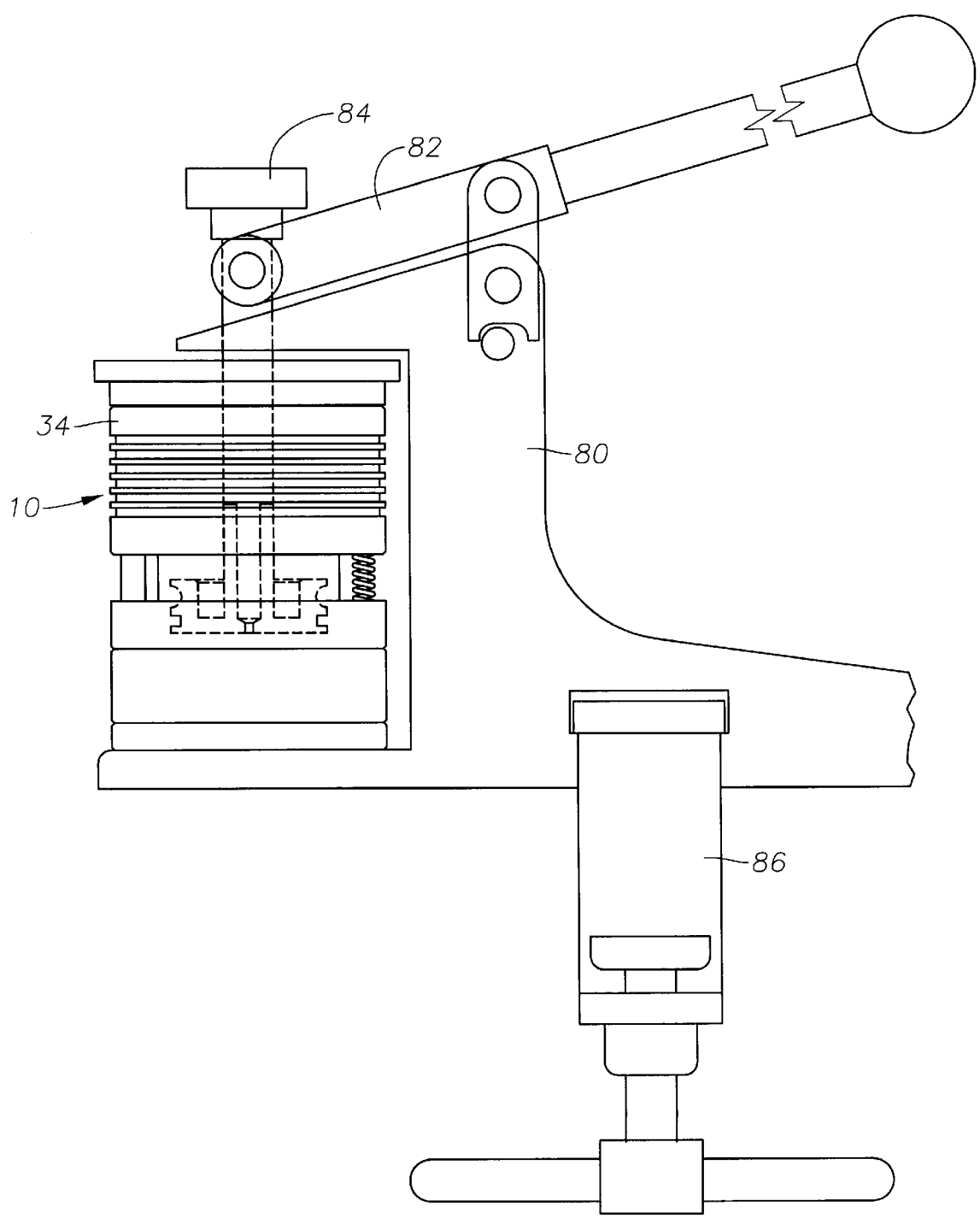
FIG. 5 illustrates a mechanical plunger to fire the particle blasting device of the FIG. 1 embodiment.

FIG. 5 illustrates a bench top holder for the device 10 of the present invention. This holder 80 basically provides a support for the IML device 10 of the present invention and is used to cock the device. In this position the device 10 may be manually fired. Manually the sleeve 34 is raised by arm 82 to cock the device. The piston is maintained in the raised position by sleeve 34. The firing of the device 10 is accomplished by using the plunger 84 to move the sleeve 34 down. The holder 80 is held on a workbench by a vice 86.

The Effect of Gravity on the IML Procedure

Utilizing the microgravity conditions created aboard NAS's KC-135 parabolic aircraft in conjunction with the IML technology, the relationship between bead impact velocity and membrane wound size and the effect of removing gravity on this cellular process were investigated. When membrane wounding is initiated during microgravity, a decrease in cell survival is observed compared to that observed in terrestrial gravity (Example 4). As bead size and impact velocity (i.e. blast pressure) were held constant in these experiments, such a decrease in cell survival during microgravity must be explained by either an increase in membrane wound size or a disruption of the resealing ability of the plasma membrane once it has been wounded. When bead impact velocity and membrane wound marker concentration are held constant, but membrane wound marker molecular size is increased, the amount of wound marker which enters the cell (MFV) during microgravity increases (Example 5) rather than decreasing as was observed in terrestrial gravity (Example 3). However, in the case of the largest membrane wound marker (i.e. 2000 kD dextran) there was no significant difference in the MFV of the surviving cell population between microgravity and terrestrial gravity. However, if wound marker size and concentration are held constant, but blast pressure is increased (i.e. increasing bead impact velocity), the MFV of the surviving population is much less in microgravity than observed in terrestrial gravity (Example 6).

EXAMPLE 4

Effect of Microgravity on Human Myoblast Cell Survival After IML

Figure 10:
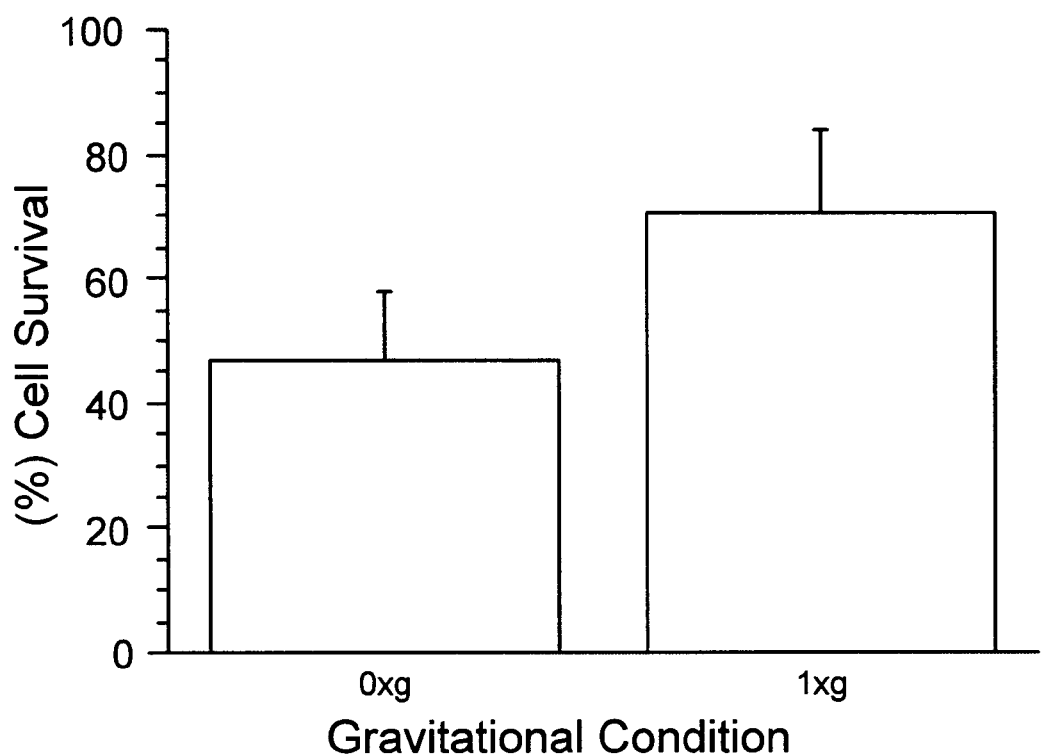
FIG. 10 is a bar graph showing the effect of human cell survival vs. terrestrial conditions and microgravity conditions.

Cells were loaded aboard the KC-135 parabolic aircraft in both terrestrial gravity (level flight) and microgravity (parabolic flight). In FIG. 10, cell survival is expressed as a (%) relative to the number of cells present in control samples which were treated in an identical fashion to the test cultures but which were not impacted with glass beads, including being flown aboard the KC-135 aircraft. Cell number was determined by measuring cellular DNA. (Bead size=8 $\mu$m dia., n=20 per condition)

EXAMPLE 5

Figure 11:
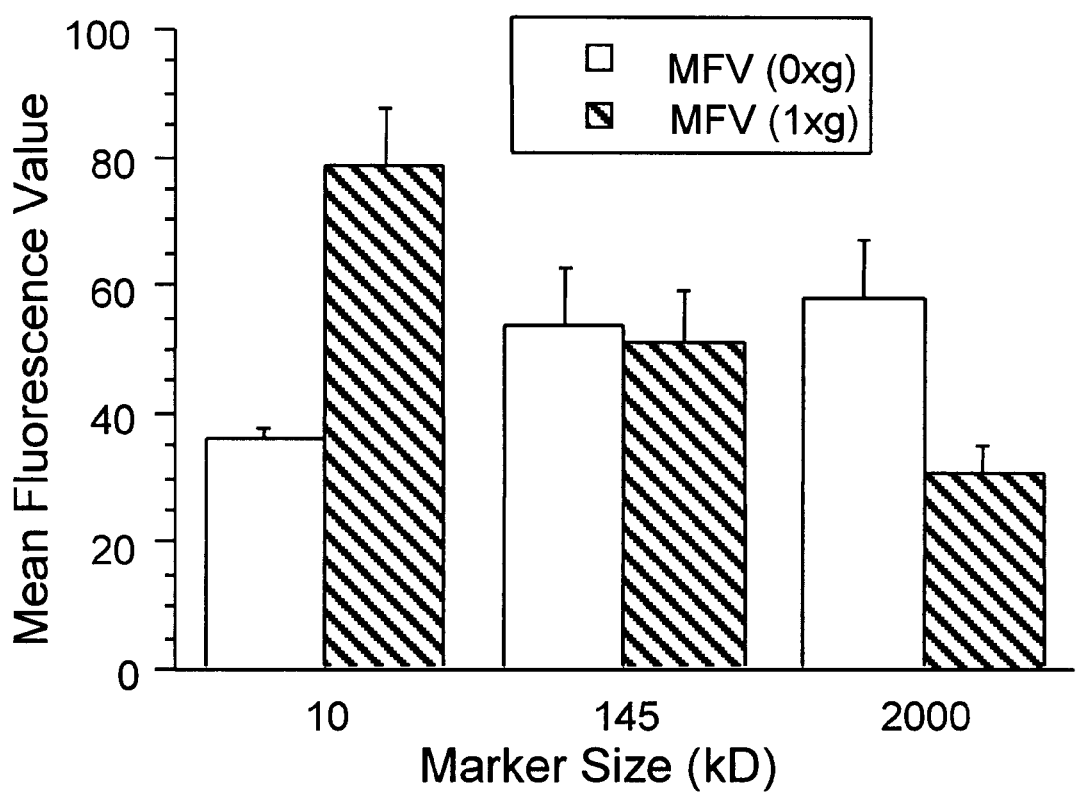
FIG. 11 is a bar ghaph showing the effect of human cell Mean Fluorescence Value under both terrestrial conditions and microgravity conditions vs. Marker Size.

Effect of Microgravity on Human Myoblast Mean Fluorescence Value (MFV) After IML in the Presence of Different Sized Membrane Wound Markers Cells were loaded during microgravity (parabolic flight–0 xg) or terrestrial gravity (level flight–1 xg) aboard the KC-135 aircraft in the presence of 0.2 mM FDx (MW–10 kD, 145 kD and 2000 kD) under identical IML conditions. Cells were returned to the laboratory, washed with fresh culture medium and harvested after a further 16 hr in culture to ensure that only the surviving population was analyzed. MFV was determined; as shown in FIG. 11, using fluorescent flow cytometry as previously described (Clarke et al., 1994, above). (Bead size=8 $\mu$m dia. Blast Pressure=35 psi; n=8 per condition).

EXAMPLE 6

Effect of Microgravity on Human Myoblast Mean Fluorescence Value (MFV) After IML at Different Particle Impact Velocities (Expressed as a Function of Blast Pressure)

Figure 12:
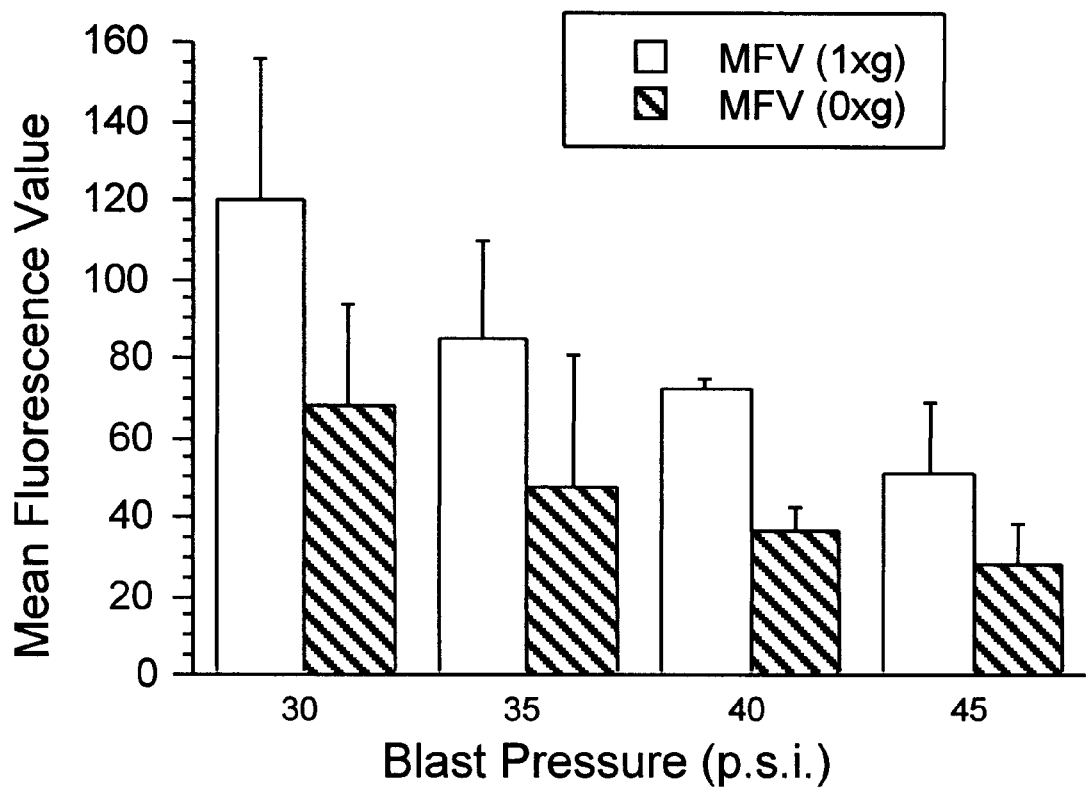
FIG. 12 is a bar ghaph showing the effect of human cell Mean Fluorescence Value under both terrestrial conditions and microgravity conditions vs. Blast Pressure.

Cells were loaded during microgravity (parabolic flight–0 xg) or terrestrial gravity (level flight–1 xg) aboard the KC-135 aircraft in the presence of 0.2 mM FDx (MW–10 kD; n=4 per condition) at different blast pressures (Bead size=8 $\mu$m dia.). Cells were returned to the laboratory, washed with fresh culture medium and harvested after a further 16 hr in culture to ensure that only the surviving population were analyzed. MFV was determined; as shown in FIG. 12, using fluorescent flow cytometry as previously described (Clarke et al., 1994, above).

The results in Examples 4 to 6 suggest that the major phenomenon responsible for the decrease in cell survival of membrane wounding in microgravity compared to cell survival in terrestrial gravity is the inhibition of resealing of the plasma membrane. This conclusion is reached rather than a conclusion that a significant increase in the size of the membrane wound is created in microgravity for a given particle size and impact velocity. This conclusion of plasma membrane resealing is based upon the relationship between membrane wound size and particle impact velocity derived in terrestrial gravity. If membrane wound size for a given particle size and impact velocity is greater in microgravity than terrestrial gravity then the MFV of the surviving cell population as particle impact velocity increases would always be greater in microgravity than in terrestrial gravity. However, this was not found to be the case (FIG. 12). However, if plasma membrane resealing is inhibited in microgravity, overall cell survival would decrease (FIG. 10), the amount of membrane wound marker which enters the cell would increase regardless of wound marker size (FIG. 11) (up to a threshold level at which the time the wound remains open would result in cell death), and as wound size increases as a consequence of increasing particle impact velocity, fewer wounded cells would survive, thereby decreasing the MFV of the surviving population (FIG. 12). As can be seen from the experimental results, the explanation which best fits the experimental observations is that microgravity inhibits plasma membrane resealing after membrane rupture. These results, the effects of microgravity upon plasma membrane wounding and other membrane-based cellular processes such as membrane-membrane fusion events (i.e. integral to membrane wound resealing), have led to the hypothesis that the removal of gravity from living cells is responsible for a disruption in the molecular ordering of constituent lipid molecules in the plasma membrane. Further that the biophysical properties of the plasma membrane are directly altered by the gravitational conditions to which the three-dimensional lipid matrix of the membrane is subjected.

Figure 13:
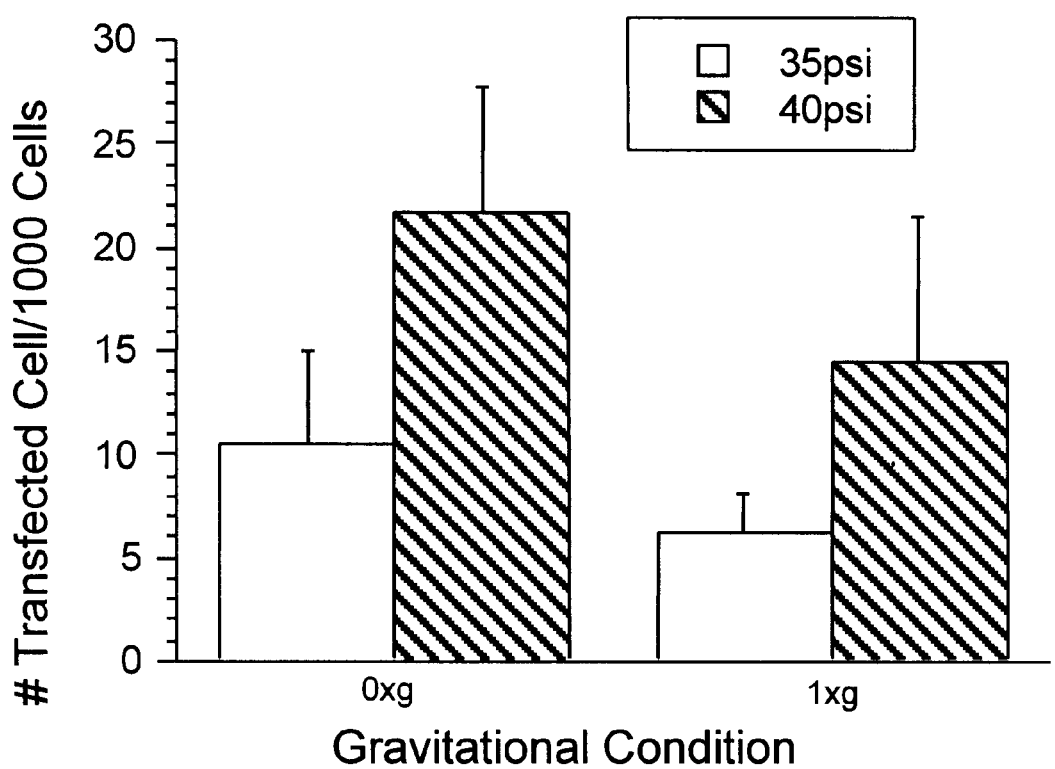
FIG. 13 is a bar graph showing the number of Transfected Cells/1000 cells at two blast pressures vs. both terrestrial conditions and microgravity conditions.

The possibility that altered gravitational conditions could be utilized to enhance the overall transfection efficiency in cultured human primary myoblast cells was investigated utilizing the IML technology as a transfection methodology (i.e. the insertion into a living cell of a plasmid DNA construct in order to express the protein encoded for by the gene embedded in the plasmid construct). This cell type was chosen due to the intense interest in being able to genetically modify this cell type as a form of gene therapy in a number of human genetic diseases, such as Duchenne's muscular dystrophy. Using marker plasmids which express non-human proteins which can then be detected later in order to assess transfection efficiency, the effect of microgravity upon transfection efficiency in human myoblasts using the pSVP (plasmid encoding the bacterial β-galactosidase enzyme) and pSVCAT (plasmid encoding the choline acetyltransferase enzyme) was investigated. Using these marker plasmids an increase in transfection efficiency was detected if either plasmid is loaded into the cell cytoplasm via a membrane wound initiated during microgravity. As plasmid DNA is an extremely large molecule (above 4000 kD if expressed in molecular size units), any procedure which creates a larger membrane wound under a constant gravitational condition, such as increased blast pressure, or allows a greater period of time for the molecule to enter the cell through the membrane wound (i.e. membrane wounding during microgravity), will theoretically increase transfection efficiency. Based upon these predictions, it was determined that transfection efficiency of human myoblast cultures can be increased by a factor of two-fold in microgravity relative to that obtained using the IML technology in terrestrial gravity (FIG. 13).

EXAMPLE 7

Effect of Microgravity on Human Myoblast Transfection Efficiency After IML at Different Particle Impact Velocities (Expressed as a Function of Blast Pressure)

Cells were impact loaded during microgravity (parabolic flight–0 xg) or terrestrial gravity (level flight–1 xg) aboard the KC-135 aircraft in the presence of 400 ug/ml pSVβ marker plasmid at different blast pressures (Bead size=8 µm dia.). Cells were returned to the laboratory, washed with fresh culture medium and histochemically stained for the presence of the bacterial β-galactosidase enzyme after a further 48 hr in culture. The results are shown in FIG. 13.

The Benefits of Hypergravity to the IML Procedure

Figure 14:
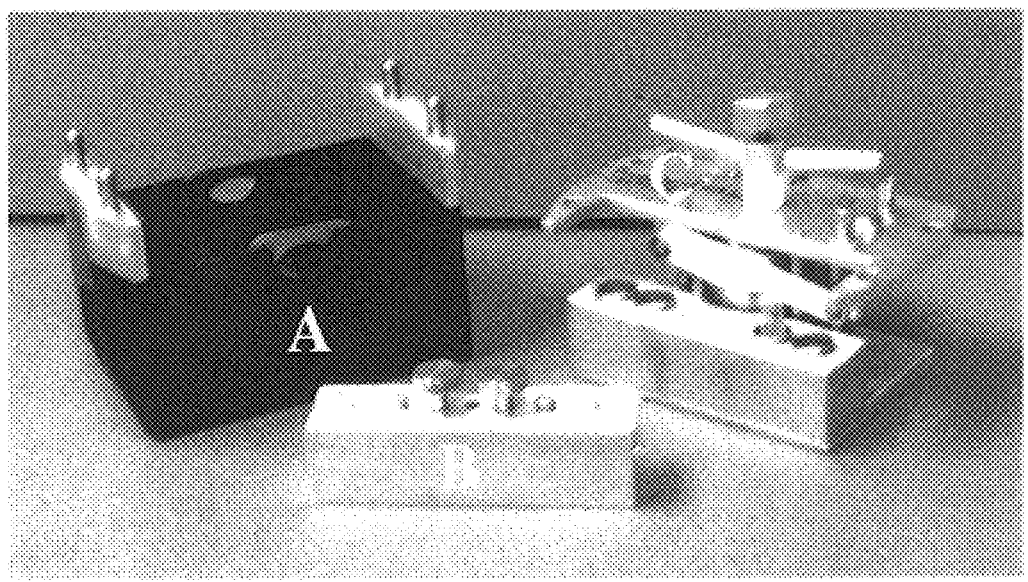
FIG. 14 is a picture of the HGIML device.
Figure 15:
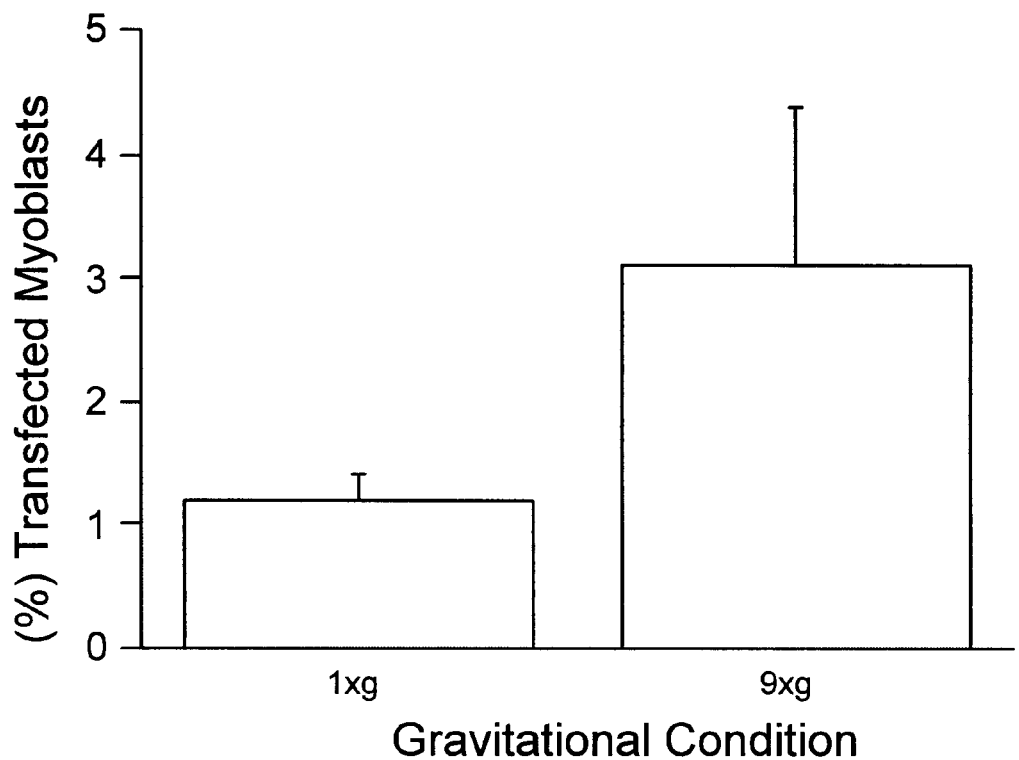
FIG. 15 is a bar graph showing the number of Transfected Microblasts vs. two gravitational conditions.
Figure 16:
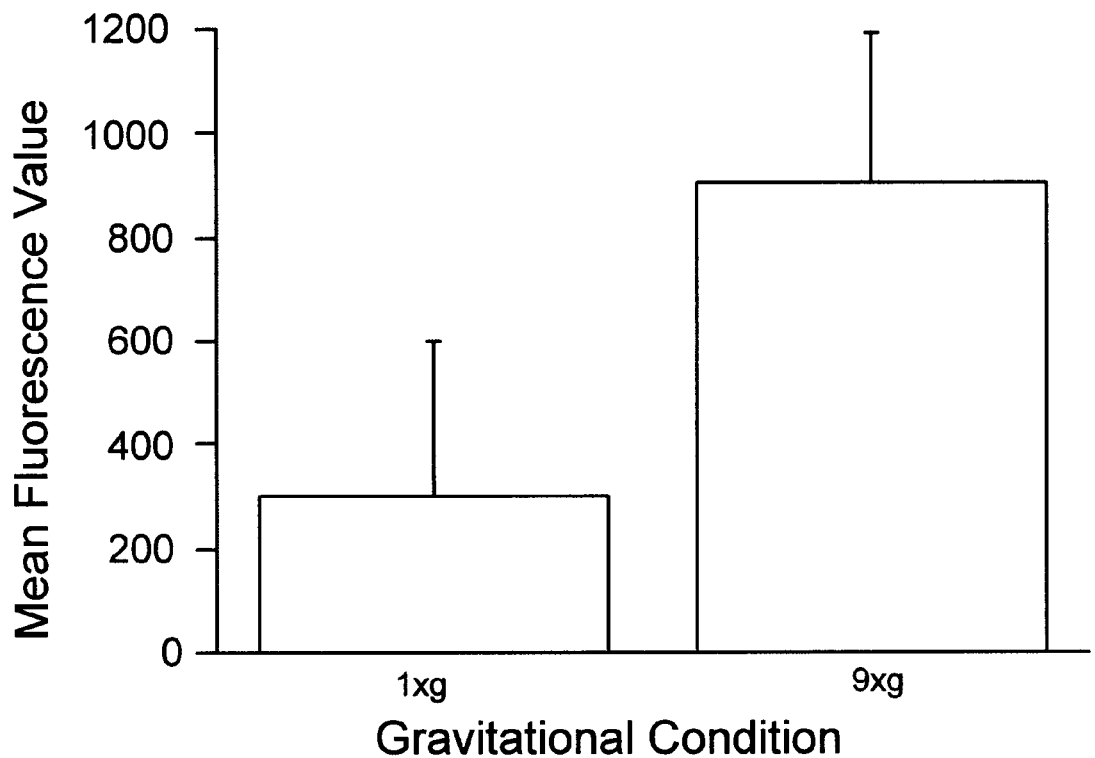
FIG. 16 is a bar graph showing Mean Fluorescence Value vs. vs. two gravitational conditions.

Based upon preliminary results obtained during the hypergravity phase (1.8 xg) of the KC-135 parabolic flight pattern, which indicated that hypergravity may also affect membrane dynamics, the effects of hypergravity upon plasma membrane wounding and transfection efficiency were investigated. In order to conduct these experiments in a controlled hypergravity environment we designed and constructed a hypergravity-operated IML (HGIML) device which is capable of initiating membrane wounding at a range of different gravity loads by virtue of operating in a swing bucket centrifuge (FIG. 14). All experiments have been conducted at 9 xg using the prototype HGIML device, a gravity load that could be reproducibly obtained in a short period of time using our experimental system. When membrane wounding is initiated at 9 xg in the presence of the marker plasmid pSVLG (a plasmid which encodes for the fluorescent protein Lantern Green™), transfection efficiency can be determined by fluorescent flow cytometry as previously used for fluorescently labeled dextran wound markers (Clarke et al., 1994, above). Utilizing this HGIML technique, transfection of human primary myoblasts is significantly increased (i.e. three-fold) over the transfection levels detected if the HGIML device is operated in terrestrial gravity (FIG. 15). In addition, the MFV of the transfected cells (a measure of how many copies of the pSVLG plasmid entered the cell) is also significantly increased (i.e. three-fold) over that detected if the cells were transfected using the HGIML device operated in terrestrial gravity (FIG. 16).

HGIML DEVICE

The HGIML device used in the following examples is illustrated in FIG. 14. (A) is a modified centrifuge bucket into which the HGIML device is placed. At the bottom of the centrifuge basket is a tissue culture plate (24-well plastic tissue culture plate). (B) is a manifold that connects to the gas chamber and supplies a blast of propellant gas to four bullet chambers (see similar sized and shape element behind). (C) is the particle blasting device with a single propellant gas chamber. The triggering structure is similar to that of FIG. 1; however, with this device a given level of hypergravity triggers the device; e.g., the sleeve is forced by gravity to the triggering position rather than by manual activation. The particles used in these examples were glass beads of 8-micron diameter. The particle containment shell had a polyethylene membrane of about 1.5 mil thickness.

EXAMPLE 9

Effect of Hypergravity (9 xg) on Human Myoblast Transfection Efficiency After IML Transfection efficiency in FIG. 15 is expressed as a (%) of the total cell population. Cells were impact loaded during hypergravity (centrifuge–9 xg) or terrestrial gravity (bench top–1 xg) in the presence of 400 ug/ml pSVLG marker plasmid (Bead size=8 µm dia.; n=5 per condition). Cells were removed from the HGIML device, washed with fresh culture medium and cultured for after a further 48 hr. They were then removed from their culture substratum by trypsinization and analyzed by fluorescent flow cytometry for the presence of the fluorescent protein Lantern Green.

EXAMPLE 10

Effect of Hypergravity on Human Myoblast Mean Fluorescence Value (MFV) After IML with pSVLG Cells were impact loaded during hypergravity (centrifuge31 9 xg) or terrestrial gravity (bench top–1 xg) in the presence of 400 ug/ml pSVLG marker plasmid (Bead size=8 µm dia.; n=4 per condition). Cells were removed from the HGIML device, washed with fresh culture medium and cultured for after a further 48 hr. They were then removed from their culture substratum by trypsinization and analyzed by fluorescent flow cytometry to quantify the amount of the fluorescent protein Lantern Green present in transfected cells. Results are shown in FIG. 16.

Figure 17:
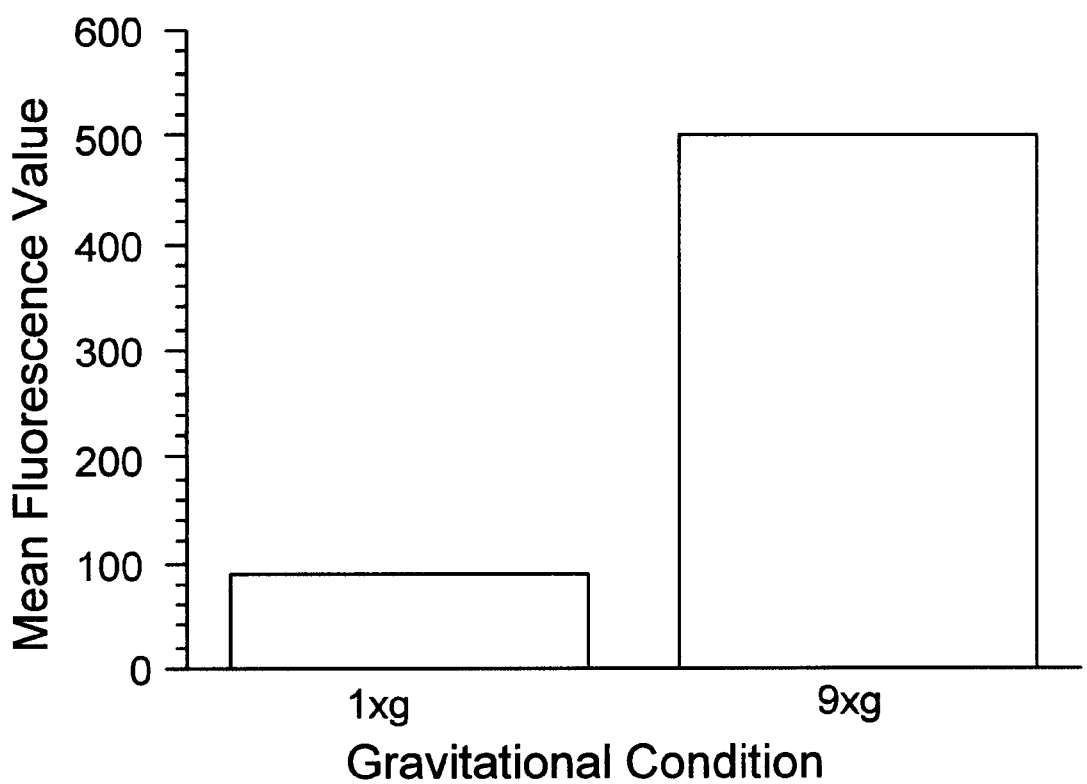
FIG. 17 is a bar graph showing Mean Fluorescence Value vs. vs. two gravitational conditions.

In addition to primary human myoblasts, several other cell types that have proved resistant to transfection by other means have been successfully transfected using the HGIML device, including human lung epithelial cells. An added advantage of the HGIML technology is that suspension cells, such as human lymphoblastic cells, can be loaded with macromolecules (including plasmid DNA). Under hypergravity conditions (9 xg) these cells are immobilized against the bottom of the culture chamber or well and behave essentially as a cell monolayer of adherent cells, the configuration/cell type required for the efficient loading of macromolecules in terrestrial gravity using the IML At technology. The percentage of cells loaded with the membrane wound marker, FDx (MW–10 kD) in terrestrial gravity was less than 1% of the population as compared to 7% of the population if these suspension cells were loaded at 9 xg using the centrifuge prototype HGIML device. In addition, the amount of marker that entered the cells was much greater under hypergravity conditions than if loading was carried out under terrestrial gravity conditions (FIG. 17.).

EXAMPLE 11

Effect of Hypergravity on Human Lymphoblastic Suspension Cells Mean Fluorescence Value (MFV) After IML Cells were impact loaded during hypergravity (centrifuge–9 xg) or terrestrial gravity (bench top–1 xg) in the presence of 0.2 mM FDx (Bead size=8 μm dia.). Cells were removed from the HGIML device, washed by centrifugation with fresh culture medium and cultured for a further 16 hr. They were then again washed by centrifugation in fresh medium and analyzed by fluorescent flow cytometry. Results are shown in FIG. 17.

As wound size and wound resealing times have an upper limit above which cell death ensues, it is essential to be able to control all experimental parameters which can affect the membrane wound process. Experimental parameters, such as the concentration of the macromolecule to be loaded, and the amount of macromolecule-containing loading solution that covers the cells are easily controlled and can be determined in a mechanistic fashion. However, the ability to control other important experimental parameters (i.e., particle size, impact velocity and gravitational conditions) involved in achieving efficient macromolecular loading using the IML technology, make the HGIML device an extremely efficient and reproducible method for cytoplasmic loading of a variety of macromolecules, including among others, plasmid DNA. The HGIML technology of the present invention combines ease of use and the ability to select loading parameters in a mechanistic fashion to a wide range of cells (i.e. both plant and animal, suspension or adherent cell types). This makes the HGIML device and associated technology suitable for a wide variety of applications in contemporary cell biology.

Alternative Embodiments

Figure 6:
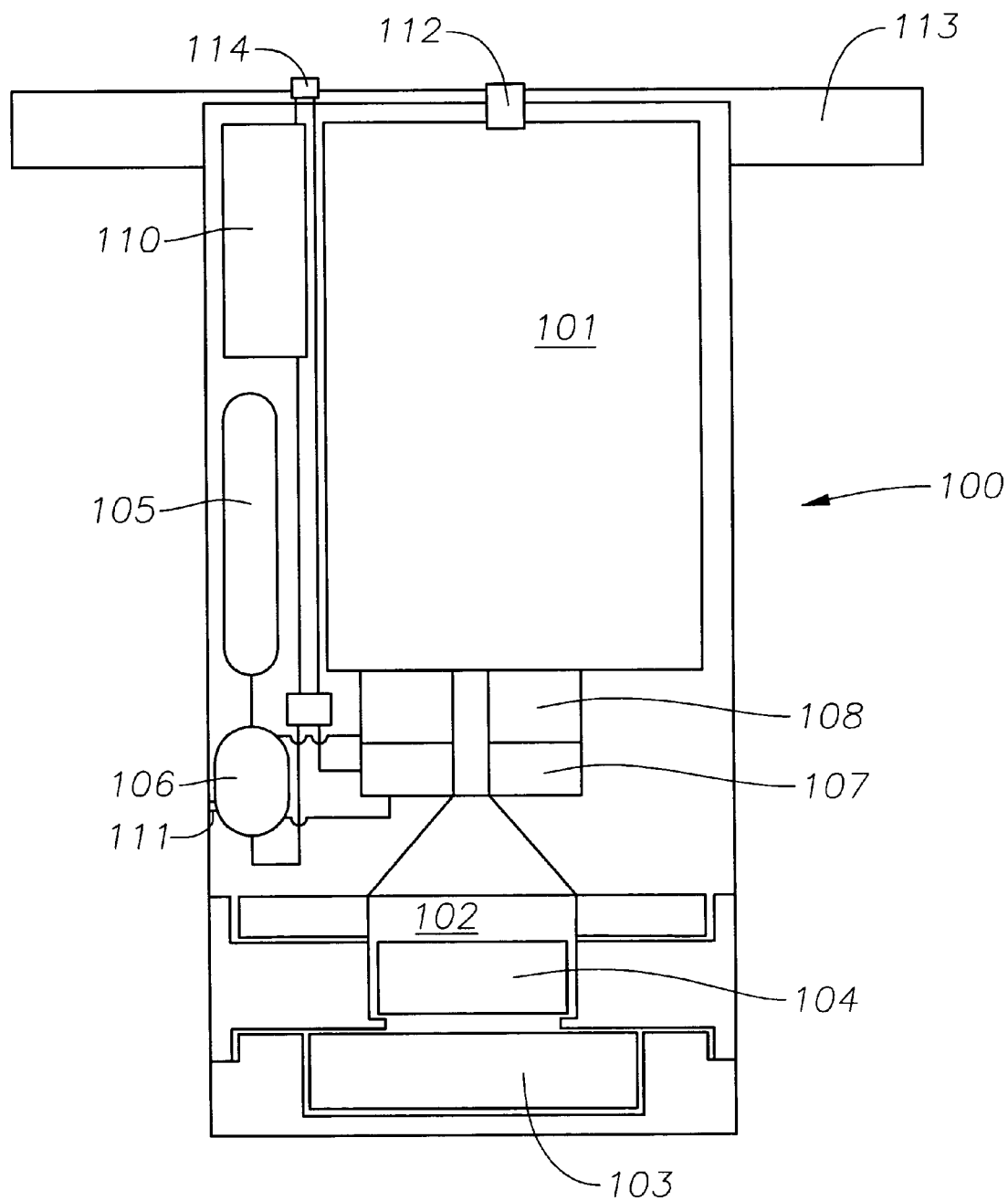
FIG. 6 illustrates a solid state electrical mechanism for firing a particle blasting device as another embodiment of the present invention and which uses a pressurized propellant gas cylinder.

Referring now to FIG. 6, another embodiment of the present invention illustrates a solid state electronic design. The HGIML device of FIG. 6 allows control of bead impact velocity by controlling blast pressure. In this device 100, there is a pressurized propellant gas chamber 101 and a bullet chamber 102. A tissue culture plate 103 is in direct line of the bullet chamber 102. A bullet or bullet assembly 104 is placed in the chamber 102. In this embodiment, an electronic circuit triggers the device. A solid state accelerometer 105 activates the circuit when a predetermined gravity is reached. The voltage change from the accelerometer activates the logic/memory chip 106 that opens the electronic valve 107 for a set period of time and at a controlled pressure as controlled by electronic pressure regulator 108. A blast of propellant gas from chamber 101 is blasted through the bullet 104 or more specifically the membranes 64 and 68 of the particle containment shell 60. Also shown in FIG. 6 is the power supply 110 for energizing the circuit and a data port 111 for inputting the desired information into the logic/memory chip 106. A one way pressure refill valve 112 allows the gas chamber 101 to be refilled. A retaining plate 113 is attached, allowing installation of the HGIML device into a centrifuge bucket. Alternatively, the device 100 may be used on a laboratory bench using a manual trigger switch 114 to activate the device.

The HGIML devices of the present invention can be used in a wide variety of different types of laboratory centrifuges due to their small sizes and universal mounting system. The HGIML devices can be configured to release their propellant blast at a range of g-forces (i.e. 1.1 to 10,000 xg; preferably 2–500 xg). The HGIML or IML devices of the present invention can utilize any size of particle by means of a simple interchangeable cartridge system or bullet.

We claim:

1. A method for gaining direct entry to living cell cytoplasm which comprises:
    rupturing a membrane supporting a predetermined number of solid particles with a blast of propellant gas; and
    propelling said predetermined number of solid particles in said blast of propellant gas to impact living cells to cause cell wounding and thereby gaining direct access to said living cell cytoplasm.

2. A method according to claim 1 wherein said blast of propellant gas is at a blast pressure controlled between 15 and 125 psi, by a predetermined volume of gas for a particular length of time.

3. A method according to claim 2 wherein said cells are mammalian in origin.

4. An impact-mediated loading {IML} device comprising:
    a propellant gas source;
    means to create and control the pressure and duration of a propellant blast of said propellant gas;
    means for directing said propellant blast through a chamber adapted to contain a predetermined number of solid particles supported on a membrane for insertion into said propellant blast; and
    a tissue culture plate positioned at a predetermined distance from said rupturable membrane and in the path of said propellant blast.

5. An IML device according to claim 4 wherein said means to create said propellant blast includes:
    a propellant gas chamber.

6. An IML device according to claim 5 that further includes:
    a pressure regulating valve connected to said gas chamber.

7. An IML device according to claim 5 that further includes:
    at least one chamber that is adapted to hold a replaceable particle containment shell and an opening connecting said gas chamber and said chamber.

8. An IML device according to claim 7 wherein there is a plurality of chambers and said tissue culture plate has a plurality of culture wells.

9. An IML device according to claim 5 that further includes:
    a piston in said propellant gas chamber; and
    means to fire said piston to empty said propellant gas chamber of gas and create said propellant gas blast.

10. A particle blasting device to carry out an impact-mediated loading procedure comprising:
    a propellant gas source;
    means to create and control the pressure and duration of a propellant blast of said propellant gas; and
    means for directing said propellant blast through a chamber adapted to contain a a predetermined number of solid particles supported on a membrane for insertion into said propellant blast.

11. A particle blasting device according to claim 10 wherein said propellant gas source includes:
    a gas chamber.

12. A particle blasting device according to claim 10 that further includes:
    a particle containment shell having a rupturable membrane on which solid particles are supported.

13. A particle containment shell comprising:
    a rigid support;
    a particle support membrane, which ruptures at a predetermined propellant blast pressure, maintained by said rigid support; and
    a predetermined number of solid particles on the surface of the support membrane.

14. A shell according to claim 13 that further includes a retaining membrane which immobilizes the solid particles on the support membrane.

15. A shell according to claim 13 wherein said solid particles are selected from the group consisting of ceramics glass, organic and inorganic crystals, metals, inorganic and organic granules, non-biodegradable polymers and biodegradable polymers.

16. A method for gaining direct entry to living cell cytoplasm which comprises:

rupturing a membrane supporting a predetermined number of solid particles with a blast of propellant gas; and propelling said predetermined number of solid particles in said blast of propellant gas under hypergravity conditions to impact living cells to cause cell wounding and thereby gaining direct access to said living cell cytoplasm.

17. A method according to claim 16 which further includes:

maintaining hypergravity conditions during and after impact to enhance the resealing of said cells.

18. A method according to claim 16 which further includes:

maintaining hypergravity conditions during and after impact to enhance the insertion of macromolecules into said cells.

19. A method according to claim 16 wherein the hypergravity conditions are between 1.1 and 10,000 xg.

20. A particle blasting device to carry out an impact-mediated loading procedure under hypergravity conditions comprising:

a propellant gas source;

means including a hypergravity trigger to create and control the pressure of and duration of a propellant gas blast; and means for directing said propellant gas blast through a chamber adapted to contain a predetermined number of solid particles supported on a membrane for insertion into said propellant gas blast.

21. A particle blasting device according to claim 20 wherein said hypergravity trigger is mechanical.

22. A particle blasting device according to claim 20 wherein said hypergravity trigger is solid state electronic.

23. A particle blasting device according to claim 22 wherein said trigger is an accelerometer.

24. A particle blasting device according to claim 21 wherein said means to create a propellant gas blast comprises:

a hydraulic cylinder tube sealed between a head and a base and a piston in said tube to form a gas chamber in a cocked position;

a sleeve surrounding said tube;

spring means mounted between said base and said sleeve to force said sleeve toward said head;

compression spring means mounted in said tube between said head and said piston to force said piston toward said base; and detent means to trigger said piston from said cocked position to empty said gas chamber.

25. A particle blasting device according to claim 24 which further comprises:

a pressure regulating valve connected to said gas chamber.

* * * * *